United States Patent [19]
Ou et al.

[11] Patent Number: 5,107,061
[45] Date of Patent: Apr. 21, 1992

[54] REMOVAL OF ORGANOCHLORIDES FROM HYDROCARBON FEED STREAMS

[75] Inventors: John D. Y. Ou; Daniel D. Rosenfeld, both of Houston, Tex.

[73] Assignee: Exxon Chemical Patents Inc., Linden, N.J.

[21] Appl. No.: 505,816

[22] Filed: Apr. 6, 1990

[51] Int. Cl.$^5$ ............................ C07C 7/12; C07C 7/13
[52] U.S. Cl. .................................. 585/823; 585/642; 585/820
[58] Field of Search ..................... 585/641, 642, 820

[56] References Cited

U.S. PATENT DOCUMENTS

| | | |
|---|---|---|
| 3,383,430 | 7/1964 | Hutson, Jr. et al. |
| 3,862,900 | 1/1975 | Reusser. |
| 3,864,243 | 2/1975 | Reusser et al. |
| 4,216,345 | 8/1980 | Messina et al. |
| 4,384,159 | 5/1983 | Diesen et al. ............... 585/642 |
| 4,404,118 | 9/1983 | Herskovits. |
| 4,488,953 | 12/1984 | Tang et al. |
| 4,557,921 | 12/1985 | Kirsch et al. ............... 423/488 |
| 4,665,270 | 5/1987 | Brophy et al. ............... 585/642 |
| 4,719,007 | 1/1988 | Johnson et al. |
| 4,814,527 | 3/1989 | Diesen ........................ 585/642 |

FOREIGN PATENT DOCUMENTS 52-65194  5/1977  Japan ....................... 502/64

OTHER PUBLICATIONS

Journal of Applied Chemistry of USSR translation of Zhurnal Prikladnoi Khimii, vol. 43, No. 11, Nov. 1970, pp. 2477–2480.

English Language Abstract of Japanese Patent JP/52–065,194, T. Tetsuo.

*Primary Examiner*—Anthony McFarlane
*Attorney, Agent, or Firm*—Linda K. Russell; Edward F. Sherer

[57] ABSTRACT

The present invention is directed to the removal of organochlorides from hydrocarbon streams using highly crystalline molecular sieve material, such as zeolites, and particularly zeolite X in a sodium form, and the removal of organochlorides from hydrocarbon streams containing olefinic compounds using such molecular sieves in combination with alumina for the purpose of effecting a decomposition of the organochloride into a corresponding unsaturated hydrocarbon molecule and a molecule of hydrocarbon chloride wherein the hydrocarbon chloride is removed from the hydrocarbon stream by being adsorbed onto the adsorbent of the highly crystalline molecular sieve used alone, or in combination with alumina in those instances where olefinic compounds are present in the hydrocarbon stream, so that the unsaturated hydrocarbon molecule may be recovered from the resultant hydrocarbon stream containing a reduced amount of organochlorides.

22 Claims, 1 Drawing Sheet

REMOVAL OF ORGANOCHLORIDES FROM HYDROCARBON FEED STREAMS

Field of the Invention

The present invention relates to the removal of halogen and halogen-containing molecules from a hydrocarbon stream. More particularly, the present invention relates to the removal of chemically-combined halogens, such as chlorine, and more specifically organochlorides, from hydrocarbons. Specifically, the present invention is directed to the removal of organochlorides from hydrocarbons using molecular sieves, as well as removing organochlorides from hydrocarbon streams containing olefinic compounds using a combination of molecular sieves and alumina.

Discussion of Background and Material Information

The removal of halogens, and particularly chemically-combined halogens, such as organochlorides, from feedstreams is highly desirable in order to prevent potential catalyst deactivation as well as equipment corrosion.

Typically, hydrocarbon products contain various amounts of halogens, such as chlorines, in the form of, for example, chemically-combined halogens, such as inorganically combined chlorides and organically combined chlorides, i.e., organochlorides. The presence of organochlorides in hydrocarbon streams typically results from the introduction of organochlorides into the hydrocarbon streams during conventional processes for producing and treating hydrocarbon products. In many instances, the organochlorides may become a part of the hydrocarbon product during the reaction of the hydrocarbon streams from which the hydrocarbon product is produced, for example, because metal chloride catalysts may be used during such reactions which have a tendency to introduce chlorine into the product which is not otherwise removable by conventional techniques such as washing, using water or a caustic.

As previously indicated, if chemically-combined chlorines, such as organochlorides, are not removed from the hydrocarbon streams, the presence of organochlorides in the resultant hydrocarbon products, particularly gasoline or other fuels, can cause corrosion of processing equipment and engine parts, as well as other deleterious effects.

U.S. Pat. No. 3,862,900, REUSSER, is directed to a method for treating hydrocarbons containing chemically-combined chlorine by passing the hydrocarbons through a bed of molecular sieves of effective pore size in the range of about 7 Angstrom units to about 11 Angstrom units to remove the chemically-combined chlorine and other impurities.

U.S. Pat. No. 3,864,243, REUSSER et al., is directed to a method for treating hydrocarbons containing chemically-combined chlorine by passing the hydrocarbons through high surface area, porous alumina at ambient temperatures to remove the chemically-combined chlorine and other impurities.

U.S. Pat. No. 4,719,007, JOHNSON et al., is directed to a process for hydrotreating a hydrocarbonaceous carbon stock which involves first contacting the hydrocarbonaceous charge stock in the presence of hydrogen with a hydrogenation catalyst; then contacting the hydrotreating reaction zone effluent with an aqueous scrubbing solution; followed by introducing a resulting admixture of the reaction zone effluent and the aqueous scrubbing solution into a separation zone to provide a hydrotreated carbonaceous stream having trace quantities of hydrogenatable hydrocarbonaceous compounds, and a spent aqueous stream; and then contacting the hydrotreated hydrocarbonaceous stream with an adsorbent to remove at least a portion of the trace quantities of hydrogenatable hydrocarbonaceous compounds from the hydrotreated hydrocarbonaceous stream. In so doing, JOHNSON et al., require at least three treatments, including hydrogenation, caustic scrubbing, and adsorption in order to remove halogenated compounds from proposed feedstreams.

U.S. Pat. No. 4,404,118, HERSKOVITS, discloses that molecular sieves, such as zeolites, have been used to remove ethers, alcohols and/or water from light liquid phase hydrocarbon streams, such as streams which are rich in $C_4$ hydrocarbons. Specifically, HERSKOVITS discloses the use of zeolitic adsorbents for removing sulfur-containing compounds and/or oxygenates from such hydrocarbon streams. In addition to sulfur-containing compounds, including mercaptans and carbon disulfide, it is also disclosed that such zeolitic adsorbents are useful to remove halogenated compounds and nitrogenous compounds, as well as unsaturated hydrocarbons when considered to be contaminants in other hydrocarbon streams. Therefore, the disclosed use of zeolitic adsorbents extends to nitrogenous compounds, unsaturated hydrocarbons, oxygenated hydrocarbonaceous compounds, water, halogenated hydrocarbonaceous compounds, and sulfur-containing compounds from a process stream. As more specifically disclosed by HERSKOVITS, the zeolitic adsorbent is used to remove such compounds from a paraffinic hydrocarbon having less than 7 carbon atoms per molecule, and an olefinic hydrocarbon having less than 7 carbon atoms per molecule, such that the compounds released by the adsorbent during regeneration become part of a hydrogen-rich stream which is disclosed as being easily removed, for example, by condensation.

U.S. Pat. No. 4,216,345, MESSINA et al., is directed to processes for obtaining linear alkylbenzenes which contain a chlorine content of less than 100 ppm. As disclosed, the process involves partial chlorination of linear paraffins having from 9 to 15 carbon atoms per molecule; catalytic alkylation of benzene using the resulting mixture of chlorinated and unreacted paraffins; and fractionation by distillation, after separation of the catalyst, of the alkylation products thus obtained and recycling the unreacted paraffins recovered from the fractionation stage to the partial chlorination stage. It is disclosed that at least a part of the unreacted paraffins to be recycled to the partial chlorination stages are submitted to a purification treatment with molecular sieves. As disclosed, the recycled paraffins containing such impurities, are passed through one or more beds of molecular sieves. In general, fixed beds are used, and it is disclosed that molecular sieves based on zeolites are particularly useful, with specific molecular sieves of the type X and of the type Y having a pore size varying between about 9 Angstrom units and 10 Angstrom units being preferred.

U.S. Pat. No. 3,383,430, HUTSON, Jr. et al., is directed to the removal of primary haloalkanes which are present in alkylate products as impurities, by contacting the alkylate with a molecular sieve to selectively adsorb the haloalkanes. It is disclosed that the primary haloalkanes can be desorbed from the molecular sieve and recovered as a second high purity product of the process.

U.S. Pat. No. 4,488,953, TANG et al., is directed to a process for the purification of recycled paraffins in a mono-chlorination process which involves the removal of polar compounds, such as phenol, substituted phenols, amines and the like using an adsorption process which uses metal oxides as the adsorbents.

Belgium Patent No. 762 502, CELANESE CORP., is directed to the purification of hydrocarbons containing an organic chloride as an impurity which involves passing the organic chloride-containing hydrocarbon at a temperature of at least 50° C. through a bed of solid dry particles whose surface contains at least one material selected from the group consisting of aluminum, magnesium, calcium, sodium and potassium. Although such metal oxides were disclosed as being useful for this purpose, there was no disclosure that zeolites, much less zeolites used alone or combined with alumina, would be particularly suitable for this purpose.

Japanese Patent 61-051-009-A is directed to the purification of polybutene by the removal of chlorinated polybutane using alumina.

SUMMARY OF THE PRESENT INVENTION

In general, the present invention is based on the discovery that molecular sieves are capable of removing organochlorides from hydrocarbons. More specifically, the present invention is based on the discovery that the effectiveness of chloride removal from hydrocarbon streams containing olefinic compounds is improved by the combined use of alumina and molecular sieves.

In accordance with the present invention, molecular sieves used alone or in combination with alumina function as a catalyst to first decompose the organochloride molecule which may be present in the hydrocarbon stream into a corresponding unsaturated hydrocarbon molecule, and a molecule of hydrogen chloride; the chloride is then removed by the adsorbent which adsorbs the hydrogen chloride. The unsaturated carbon, however, is not adsorbed by either the zeolite or the alumina but passes through the decomposition zone and may be recovered in the product stream.

In a preferred embodiment, the present invention is directed to the removal of organochlorides from hydrocarbon streams containing olefinic substances by subjecting the olefinic stream to a highly-crystalline molecular sieve and alumina under conditions suitable for decomposing the organochloride into its corresponding unsaturated hydrocarbon molecule and a molecule of hydrogen chloride; adsorbing the hydrogen chloride; and recovering the corresponding unsaturated hydrocarbon from the product stream.

BRIEF DESCRIPTION OF THE DRAWING

The Figure is a flow chart for the adsorption process the present invention.

DETAILED DESCRIPTION OF THE INVENTION

Figure 1:
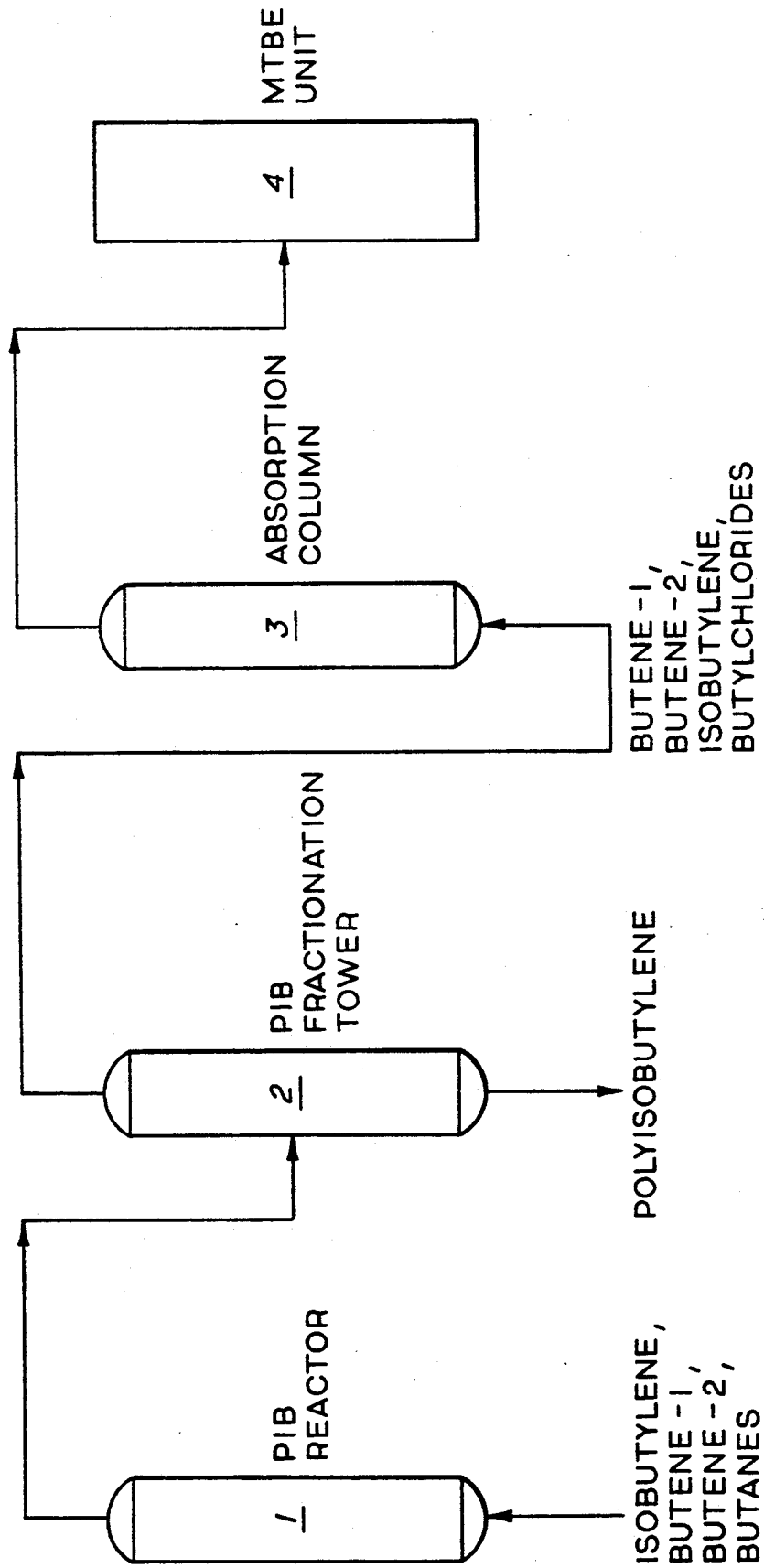

The present invention involves removing chemically-combined halogens, such as organochlorides, from hydrocarbon streams containing organochlorides, by contacting the hydrocarbon stream containing organochlorides with appropriate catalytic materials for a time and under conditions sufficient to decompose the organochloride molecule into a corresponding unsaturated hydrocarbon molecule and a molecule of hydrogen chloride which is then adsorbed by a molecular sieve so as to effect chloride removal from the hydrocarbon stream.

The present invention is also directed to removing organochlorides from a hydrocarbon stream containing olefinic compounds and organochlorides by contacting the hydrocarbon stream with a highly crystalline molecular sieve material and alumina for a time and under conditions suitable for decomposing the organochloride molecule into a corresponding unsaturated hydrocarbon molecule and a molecule of hydrogen chloride. The hydrogen chloride is then adsorbed by the molecular sieve material and alumina; subsequently, the unsaturated hydrocarbon is recovered from the resultant purified hydrocarbon stream.

For purposes of the present invention, molecular sieves having an effective pore size of from about 5 Angstrom units to about 15 Angstrom units are suitable; however, molecular sieves having an effective pore size within the range of about 7 Angstrom units to about 10 Angstrom units are preferred, with molecular sieves having an effective pore size within the range of about 10 Angstrom units being more preferred. Highly crystalline molecular sieves are preferred for removing organochlorides from hydrocarbon streams, with zeolites being most preferred.

The zeolite preferred for purposes of the present invention has a pore size within the range of about 5 Angstrom units to about 15 Angstrom units, and may be in the form of crushed or beaded particles. For purposes of the present invention include zeolite X, Y, A, beta and mordenite are the more preferred zeolites. However, zeolite X, i.e., sodium X zeolite, is the most preferred zeolite. Zeolite X molecular sieves are described in U.S. Pat. No. 2,883,244, a specific example which is disclosed in U.S. Pat. No. 3,862,900, the disclosures of which are hereby incorporated by reference herein thereto.

Properties of zeolites suitable for this application are described, for example, in "Zeolite Molecular Sieves" by D. W. Breck, R. E. Krieger Publishing Co., 1984. The zeolites are commercially available from UOP Inc. Properties of some zeolites are listed below:

Zeolite X

Average composition: $Na_2O \cdot Al_2O_3 \cdot 2.5SiO_2 \cdot 6H_2O$
Pore Diameter: ~10 A
Reference: R. M. Milton, U.S. Pat. No. 2,882,244 (1959)

Zeolite Y

Average composition: $Na_2O \cdot Al_2O_3 \cdot 4.8SiO_2 \cdot 8.9H_2O$
Pore Diameter ~10 A
Reference: D. W. Breck, U.S. Pat. No. 3,130,007 (1964)

Zeolite A

Average composition: $0.25Na_2O \cdot 0.75CaO\ Al_{0.2}O_3 \cdot SiO_2\ 4.5H_2O$
Pore Diameter: ~5 A
Reference: R. M. Milton, U.S. Pat. No. 2,882,243 (1959)

Zeolite Mordenite

Average composition: $Na_2O \cdot Al_2O_3 \cdot 9-10SiO_2 \cdot 6H_2O$
Pore Diameter: ~7 A Reference: R. M. Milton, U.S. Pat. No. 2,882,244 (1959)

The present invention is also based on a discovery that, in the presence of olefinic compounds, the effectiveness of chloride removal may be improved by the combination of alumina with the molecular sieves. In this regard, the removal efficiency has been discovered to be improved by combining alumina adsorbent and zeolitic adsorbent in series or in a mixture.

Alumina suitable for purposes of the present invention may be selected from conventional alumina adsorbents which have appropriate high adsorptive power, a high surface area, suitable hardness, resistance to crumbling during handling and use, suitable size and granular form. A representative example of alumina suitable for purposes of the present invention is disclosed in U.S. Pat. No. 3,864,243, the disclosure of which is hereby incorporated by reference herein thereto. The following description relates to alumina suitable for purposes of the present invention.

Kaiser Activated Alumina A-201 (neutral)

| 8 × 14 mesh spheres with a high surface area (325 m²/gm) | |
|---|---|
| Typical analysis | 93.25% $Al_2O_3$ |
| (dry basis) | 0.35% $Na_2O$ |
| | 0.02% $Fe_2O_3$ |
| | 0.02% $SiO_2$ |

In accordance with the present invention, alumina has been found to be particularly effective in decomposing tertiary chlorides, while zeolite has been used to dehydrohalogenate primary and secondary chlorides.

The hydrocarbon stream including the organochloride treated in accordance with the present invention preferably includes olefin compounds, and the material effective to decompose the organochloride is a combination of Na X zeolite and said alumina. The olefinic compounds present in the hydrocarbon stream are selected from the group consisting of mono-olefins, polyolefins, linear olefins, branched olefins, alpha olefins and internal olefins. The hydrocarbon stream treated in accordance with the present invention may also include hydrocarbons selected from the group consisting of aromatics and paraffins as well as olefins. The organochlorides removed from the hydrocarbon stream in accordance with the present invention are selected from the group consisting of primary alkyl chlorides, secondary alkyl chlorides, tertiary alkyl chlorides, and allyl chlorides, and preferably are selected from the group consisting of primary butyl chlorides, secondary butyl chlorides and tertiary butyl chlorides.

In a preferred embodiment of the present invention, the step of exposing the hydrocarbon stream to the previously described materials involves dehydrohalogenating the primary butyl chlorides and the secondary butyl chlorides over an Na X zeolite and decomposing the tertiary butyl chlorides over alumina, preferably wherein the step involves subjecting the hydrocarbon stream to the Na X zeolite and the alumina in series. The process of the present invention also involves recovering the unsaturated hydrocarbon product stream from which the hydrogen chloride has been removed.

In another preferred embodiment, the organochlorides which are removed preferably include secondary butyl chlorides and tertiary butyl chlorides, and the process of the present invention also involves recovering the unsaturated hydrocarbon molecule from a resultant hydrocarbon product stream from which the hydrogen chloride has been removed, wherein the hydrocarbon feed stream includes the secondary butyl chlorides and the tertiary butyl chlorides at levels up to about 0.2%, and the resultant hydrocarbon product stream includes reduced amounts of the secondary butyl chlorides and the tertiary butyl chlorides at levels below about 1 ppm.

The process of the present invention is performed under conditions including temperatures within the range of about 10° C. to about 100° C. and pressures within the range of about ambient to about 500 psi; preferably the temperatures are within the range of ambient temperatures of 15° C. to about 65° C.

The hydrocarbon stream containing organochlorides treated in accordance with the present invention may be produced or otherwise obtained from conventional procedures. For example, streams of hydrocarbons that have been found to contain organochlorides include paraffins from isomerization processes, olefins from isomerization processes, olefins from polymerization processes, and the like. Also, processes utilizing a chloride-base catalyst to isomerize linear paraffins to branched paraffins could produce a small amount of alkylchlorides in the product streams. Chloride-base catalysts are also frequently used for olefin polymerization processes such as polybutene process and polyisobutylene process. Contaminants of organochlorides in the form of monomers or polymers have been observed in the product streams.

The present invention is particularly suitable for removing organochlorides from hydrocarbons containing olefinic compounds. The problem of removing organochlorides from hydrocarbon streams containing olefinic compounds occurs in the case of utilizing the raffinate stream for a polyisobutylene (PIB) process. The process uses aluminum chloride to catalyze the polymerization of isobutylene to PIB. In addition to isobutylene, the charge stock to the reactor usually contains butene-1, butene-2 and butanes. Ideally, the catalyst would only polymerize isobutylene and leave other compounds unscathed. These compounds and unreacted isobutylene would then separated from PIB by distillation and used for other applications. However, the raffinate stream from the PIB distillation column is usually contaminated with butyl chlorides due to reactions between aluminum chloride and butenes, and such a raffinate stream contaminated with butyl chlorides cannot, therefore, be used for productions of MTBE, butene-1, butene-2, and the like.

In addition to the foregoing, the process of the present invention is applicable removing organochlorides from hydrocarbons produced by other conversion processes, such as isomerization, and polymerization, that yield a hydrocarbon effluent containing chemically-combined chlorines, such as organochlorides.

As previously discussed, the present invention is directed to the removal of organically-combined chlorine, i.e., organochlorides, from hydrocarbon streams containing organochlorides by subjecting the hydrocarbon stream to appropriate catalytic materials for a time and under suitable conditions effective to decompose the organochloride into its unsaturated hydrocarbon molecule and a molecule of hydrogen chloride, the latter of which is then adsorbed by an adsorbent effective for this purpose. For example, in accordance with the present invention, a raffinate stream from PIB distillation column, which typically contains 50% n-butane, 30% butene-1, 15% butene-2, 3% iso-butylene, 2% isobutane, 50-100 ppm secondary butyl chloride, and 5-10 ppm tertiary butyl chloride, is introduced into an adsorption column packed with zeolite adsorbent, such as zeolites X, Y, beta, and mordenite, at a temperature ranging from ambient to about 100° C., a pressure from ambient to about 500 psig, and a flow rate from about 0.5 to about 5 LHSV (Liquid Hourly Space Velocity). The adsorbent decomposes secondary butyl chloride into n-butene and hydrogen chloride and the resultant n-butene is released from the adsorbent pores and recovered in the column effluent. Hydrogen chloride, however, is adsorbed by the adsorbent and eliminated from the stream. The removal mechanism for tertiary butyl chloride is similar except that isobutylene instead of n-butene is formed.

The single figure of the accompanying drawing, which is presented as a representative example of the present invention for illustrative purposes and is not meant to limit the present invention to the details shown and described, is a flowsheet of the process for the removal of organochlorides in accordance with the invention.

As shown, the charge stock (containing normal butenes, isobutylene, butanes, and low level of butyl chlorides and polyisobutylene) to be treated for chloride removal is the raffinate stream from the fractionation tower 2 of a polyisobutylene unit 1. The stream is introduced into the adsorption column 3, where it is contacted with the adsorbent for the purpose of dehydrochlorinating the organochlorides and adsorbing the resultant hydrogen chloride. The effluent from the adsorption column, which contains less than 1 ppm chloride, can be used as feed stock for a down-stream methyl tertiary butyl ether (MTBE) unit 4.

The present invention has been found to be particularly useful in removing organochlorides present in the hydrocarbon stream in relatively small amounts.

EXAMPLES

The following non-limiting examples are given by way of illustration of the present invention.

EXAMPLE I

The following example is given to evidence that the organochloride present in the hydrocarbon stream is first decomposed into a corresponding unsaturated hydrocarbon molecule and a molecule of hydrogen chloride wherein the hydrogen chloride is removed by adsorption onto the molecular sieve and the unsaturated hydrocarbon molecule is recovered in the effluent product stream.

Three zeolite adsorbents including sodium-X, calcium-X and barium-X were tested for butyl chlorides removal. The feed solution was a mixture of 0.461% secondary butyl chloride, 0.036% tertiary butyl chloride, and 99.503% n-heptane. There were no butenes or isobutylene in the feed solution. Ten grams of the feed solution were allowed to equilibrate with 2 grams of each adsorbent in sealed bottles at ambient temperature and pressure for 18 hours. After the equilibration, GC analysis indicated that the concentration of butyl chlorides was less than 1 ppm in all three solutions. However, low levels of n-butenes (butene-1 and butene-2) and isobutylene in the solutions were detected. Since there were no butenes initially present in the systems, the presence of these compounds and the disappearance of chlorides indicated the dehydrochlorination of butyl chlorides and the subsequent adsorption of hydrogen chloride.

EXAMPLE II

The following example is given to show that the removal efficiency of the adsorbent is improved by combining alumina adsorbent and zeolitic adsorbent in series or in a mixture, particularly for the treatment of a hydrocarbon stream containing primary, secondary and tertiary organochlorides.

Static Test

Three Parr reactors were charged with the following feed:

| FEED: | 68% unsaturated butenes, 32% saturated butanes, 45 ppm sec-butylchloride and 18 ppm tertiary butylchloride. |
|---|---|

(1) To one was also added formulated Na-X.
(2) To another was added a 1:1 mixture of Na-X and Alumina (A-201).
(3) To the third was added a 1:3 mixture of Na-X and Alumina (A-201).

Each was then heated to about 55° C. for four hours.

Analysis of the supernatent liquid indicated that the combination of Na-X and Alumina adsorbed more of the organochlorides present than did the Na-X alone:

|  | (1) | (2) | (3) |
|---|---|---|---|
| sec butylchloride | 10 ppm | 0.8 ppm | 0.6 ppm |
| ter butylchloride | 3 ppm | 0.5 ppm | 0.2 ppm |

As indicated, this example also shows that alumina is effective in decomposing the tertiary chlorides while the zeolite was effective to dehydrohalogenate primary and secondary chlorides.

EXAMPLE III

The following example illustrates the adsorption/chemisorption mechanism resulting in the generation of unsaturated hydrocarbons and hydrogen chlorides.

A break-through test was conducted to determine the capacity of sodium-X zeolite for butyl chlorides removal. The adsorbent was a clay-bound sodium-X zeolite obtained from U.O.P. Inc. It was ground to particles with sizes ranging from 30 mesh to about 60 mesh and calcined at 400° C. prior to use. The adsorbent was then loaded into a 5 cc stainless steel column.

A feed solution containing 90% n-heptane, 10% butene-1, 450 ppm secondary butyl chloride, and 90 ppm tertiary butyl chloride was pumped through the column at 65° C., 300 psig, and a flow rate of 1.2 LHSV. Column effluent was sampled periodically and analyzed for butyl chlorides and hydrogen chloride. It was found that the concentration of butyl chlorides in product was below 1 ppm until the total amount of butyl chlorides pumped through the column reached 10.5% of the weight of the sodium-X adsorbent. The concentration of hydrogen chloride in product before and after break-through was below detection limit.

As indicated, the dynamic tests conducted at 65° C. result in capacities of about 10.5% for organochlorides in heptane.

It will also be appreciated by those of ordinary skill in the art that, while the present invention has been described herein by reference to particular means, methods and materials, the scope of the present invention is not limited thereby and extends to any and all other means, methods and materials suitable for practice of the present invention. Therefore, although the present invention has been described with reference to particular means, materials and embodiments, from the foregoing description one skilled in the art can easily ascertain the essential characteristics of the present invention, and various changes and modifications may be made to various usages and conditions, without departing from the spirit and scope of the invention as described in the claims that follow.

What is claimed is:

1. A process for purifying a hydrocarbon stream containing organochlorides, said process comprising:
    exposing a hydrocarbon stream comprising an organochloride to a material selected from the group consisting of molecular sieve material, alumina material, and combinations of molecular sieve material and alumina material under conditions comprising a temperature within the range of about 10° C. to about 100° C. effective to decompose said organochloride into its unsaturated hydrocabon molecule and a molecule of hydrogen chloride, and to absorb said molecule of hydrogen chloride so as to result in a hydrocarbon stream which is substantially devoid of hydrogen chloride.

2. The process as defined by claim 1, wherein said molecular sieve material is selected from the group of crystalline molecular sieve material having a pore size within the range of 5 Angstrom units to about 15 Angstrom units.

3. The process as defined by claim 2, wherein said highly crystalline molecular sieve material is selected from a group consisting of zeolites.

4. The process as defined by claim 4, wherein said zeolites are selected from the group consisting of zeolite X, Y, A, and mordenite.

5. The process as defined by claim 4, wherein said zeolites are selected from the group of cation-exchanged zeolites.

6. The process as defined by claim 5, wherein the cations in said cation-exchanged zeolites are selected from the group consisting of alkali metals and alkaline earth metals.

7. The process as defined by claim 6, wherein said

8. The process as defined by claim 7, wherein said type X zeolite is Na X zeolite.

9. The process as defined by claim 8, wherein said hydrocarbon stream comprising said organochloride comprises olefin compounds.

10. The process as defined by claim 9, wherein said material effective to decompose said organochloride comprises a combination of said Na X zeolite and said alumina.

11. The process as defined by claim 10, wherein said olefinic compounds are selected from the group consisting of mono-olefins, polyolefins, linear olefins, branched olefins, alpha olefins, and internal olefins.

12. The process as defined by claim 8, wherein said hydrocarbon stream comprises hydrocarbons selected from the group consisting of aromatics, paraffins and olefins.

13. The process as defined by claim 12, wherein said organochloride is selected from the group consisting of primary alkyl chlorides, secondary alkyl chlorides, tertiary alkyl chlorides, and allyl chlorides.

14. The process as defined by claim 13, wherein said organochloride is selected from the group consisting of primary butyl chlorides, secondary butyl chlorides and tertiary butyl chlorides.

15. The process as defined by claim 14, wherein said exposing comprises dehydrohalogenating said primary butyl chlorides and said secondary butyl chlorides over said Na X zeolite and decomposing said tertiary butyl chlorides over said alumina.

16. The process as defined by claim 15, wherein said exposing comprises subjecting said hydrocarbon stream to said Na X zeolite and said alumina in series.

17. The process as defined by claim 16, further comprising recovering said unsaturated hydrocarbon product stream from which said hydrogen chloride has been removed.

18. The process as defined by claim 8, wherein said organochlorides are selected from the group consisting of secondary butyl chlorides and tertiary butyl chlorides.

19. The process as defined by claim 18, further comprising recovering said unsaturated hydrocarbon molecule from a resultant hydrocarbon product stream from which said hydrogen chloride has been removed.

20. The process as defined by claim 19, wherein said hydrocarbon stream comprises said secondary butyl chlorides and said tertiary butyl chlorides at levels up to about 0.2, and said resultant hydrocarbon product stream comprises reduced amounts of said secondary butyl chlorides and said tertiary butyl chlorides at levels below about 1 ppm.

21. The process as defined by claim 2, wherein said conditions comprise temperatures within the range of about 10° C. to about 100° C., and pressures within the range of about ambient to about 500 psi.

22. The process as defined by claim 2, wherein said temperatures are within the range of ambient temperatures of 15° C. to about 65° C.

* * * * *